(12) United States Patent
Qasem

(10) Patent No.: US 11,006,842 B2
(45) Date of Patent: May 18, 2021

(54) NON-INVASIVE BRACHIAL BLOOD PRESSURE MEASUREMENT

(71) Applicant: AtCor Medical Pty Ltd, West Ryde (AU)

(72) Inventor: Ahmad Qasem, Guildford (AU)

(73) Assignee: AtCor Medical Pty Ltd, West Ryde (AU)

( * ) Notice: Subject to any disclaimer, the term of this patent is extended or adjusted under 35 U.S.C. 154(b) by 406 days.

(21) Appl. No.: 15/907,693

(22) Filed: Feb. 28, 2018

(65) Prior Publication Data

US 2018/0249915 A1    Sep. 6, 2018

Related U.S. Application Data

(60) Provisional application No. 62/465,881, filed on Mar. 2, 2017.

(51) Int. Cl.
  *A61B 5/021*    (2006.01)
  *A61B 5/022*    (2006.01)
  *A61B 5/00*     (2006.01)

(52) U.S. Cl.
  CPC ...... *A61B 5/02141* (2013.01); *A61B 5/02225* (2013.01); *A61B 5/6824* (2013.01); *A61B 2560/0228* (2013.01)

(58) Field of Classification Search
  None
  See application file for complete search history.

(56) References Cited

U.S. PATENT DOCUMENTS

| | | |
|---|---|---|
| 4,796,184 A | 1/1989 | Bahr |
| 5,265,011 A | 11/1993 | O'Rourke |
| 5,882,311 A | 3/1999 | O'Rourke |
| 6,485,431 B1 | 11/2002 | Campbell |
| 6,647,287 B1 | 11/2003 | Peel et al. |
| 6,994,675 B2 | 2/2006 | Sharrock |

(Continued)

FOREIGN PATENT DOCUMENTS

| | | |
|---|---|---|
| EP | 0297146 B1 | 10/1993 |
| EP | 1179318 | 2/2002 |

(Continued)

OTHER PUBLICATIONS

Roman, et al., High Central Pulse Pressure is Independently Associated with Adverse Cardiovascular Outcome, Journal of American College of Cardiology, vol. 54, No. 18, Oct. 27, 2009, pp. 1730-1734.

(Continued)

*Primary Examiner* — Etsub D Berhanu
*Assistant Examiner* — Aurelie H Tu
(74) *Attorney, Agent, or Firm* — Andrus Intellectual Property Law

(57) ABSTRACT

A method of measuring a patient's systolic and diastolic brachial blood pressure non-invasively with a brachial cuff considers the shape of a patient's peripheral waveform (e.g., the cuff volumetric displacement waveform) to recalibrate the height of the waveform. The maximum and minimum values of the recalibrated waveform correlate to and closely estimate counterpart values for invasively measured brachial systolic and diastolic pressure.

14 Claims, 8 Drawing Sheets

(56) References Cited

U.S. PATENT DOCUMENTS

| | | | |
|---|---|---|---|
| 7,455,643 B1* | 11/2008 | Li | A61B 5/021 600/490 |
| 7,727,157 B2 | 6/2010 | Sharrock | |
| 8,100,835 B2 | 1/2012 | Baruch | |
| 8,821,403 B2 | 9/2014 | Sharrock | |
| 9,289,138 B2 | 3/2016 | Chowienczyk et al. | |
| 9,314,170 B2 | 4/2016 | Qasem | |
| 9,408,542 B1* | 8/2016 | Kinast | A61B 5/02125 |
| 2002/0156382 A1 | 10/2002 | Freund et al. | |
| 2002/0177781 A1 | 11/2002 | Amano | |
| 2003/0109776 A1* | 6/2003 | Jacques | A61B 5/1495 600/331 |
| 2003/0220584 A1 | 11/2003 | Honeyager et al. | |
| 2004/0024324 A1 | 2/2004 | Bratteli | |
| 2004/0059231 A1 | 3/2004 | Narimatso et al. | |
| 2004/0158162 A1 | 8/2004 | Narimatsu | |
| 2008/0287793 A1 | 11/2008 | Hoffman | |
| 2009/0149763 A1 | 6/2009 | Chen et al. | |
| 2009/0287097 A1 | 11/2009 | Lowe | |
| 2010/0241013 A1 | 9/2010 | Hatib | |
| 2011/0237961 A1 | 9/2011 | Voss et al. | |
| 2011/0270098 A1 | 11/2011 | Chowienczyk | |
| 2011/0275911 A1 | 11/2011 | Qasem | |
| 2011/0275944 A1* | 11/2011 | Qasem | A61B 5/7225 600/493 |
| 2012/0041279 A1* | 2/2012 | Freeman | G06F 19/00 600/301 |
| 2012/0136261 A1* | 5/2012 | Sethi | A61B 5/1495 600/485 |
| 2013/0085357 A1* | 4/2013 | Huber | A61B 5/0205 600/364 |
| 2014/0051953 A1* | 2/2014 | Lamego | A61B 5/7221 600/316 |
| 2015/0327786 A1 | 11/2015 | Lading | |
| 2017/0055854 A1* | 3/2017 | Choucair | A61B 5/6824 |
| 2018/0263513 A1* | 9/2018 | Qasem | A61B 5/02108 |
| 2018/0296104 A1* | 10/2018 | Qasem | A61B 5/02116 |

FOREIGN PATENT DOCUMENTS

| | | |
|---|---|---|
| EP | 1380254 | 1/2004 |
| EP | 2070472 | 6/2009 |
| EP | 2759258 B1 | 9/2016 |
| EP | 3130280 A1 | 2/2017 |
| WO | 2007053868 | 5/2007 |
| WO | 2010002250 | 1/2010 |
| WO | 2010058169 | 5/2010 |
| WO | 2011135446 A2 | 11/2011 |
| WO | 2016110781 A1 | 7/2016 |

OTHER PUBLICATIONS

McEniery, et al., Central Pressure Variability and Impact of Cardiovascular Risk Factors, The Anglo-Cardiff Collaborative Trial II, Hypertension, Jun. 2008, pp. 1476-1482.

Williams, et al., Differential Impact of Blood Pressure-Lowering Drugs on Central Aortic Pressure and Clinical Outcomes, Principal Results of the Conduit Artery Function Evaluation (CAFE) Study, Circulation Mar. 7, 2006, pp. 1213-1225.

Pauca, et al., Prospective Evaluation of a Method of Estimating Ascending Aortic Pressure from the Radial Artery Pressure Waveform, Hypertension, Oct. 2001, vol. 38, pp. 932-937.

Sharman, et al., Validation of a Generalized Transfer Function to Noninvasively Derive Central Blood Pressure During Exercise, Hypertension, Jun. 2006, vol. 47, pp. 1203-1208.

Wassertheurer, et al., A new oscillometric method for pulse wave analysis: comparison with a common tonometric method, Journal of Human Hypertension 24, 2010, pp. 498-504, published online Mar. 18, 1010.

Jilek, et al., Amplitude envelope slopes of oscillometric blood pressure waveforms as defined by amplitude ratios, Applied Electronics, 2009, pp. 137-140.

Mersich, et al., Identification of the cuff transfer function increases indirect blood pressure measurement accuracy, Physiological Measurement, Institute of Physics Publishing, Bristol, GB, vol. 30, No. 3, Mar. 1, 2009, pp. 323-333.

American National Standard, ANSI/AAMI/ISO 8160-2:2009, Non-invasive sphygmomanometers—Part 2: Clinical validation of automated measurement type, Section 5.2.4.1.2 Part a—Criterion 1, p. 20.

Sharman, et al., Validation of non-invasive central blood pressure devices: Artery Society task force consensus statement on protocol standardization; European Heart Journal (2017) 0, 1-10.

Cloud, et al., Estimation of central aortic pressure by SphygmoCor requires intra-arterial peripheral pressures, Clinical Science (2003) 105, 219-225.

Shoji, et al., Invasive validation of a novel brachial cuff-based oscillmetric device (SphygmoCor XCEL) for measuring central blood pressure, Journal of Hypertension 2016, 1-7.

Nichols, et al., McDonald's Blood Flow in Arteries: Theoretical, Experimental and Clinical Principles, Fifth Edition, 2005.

Roman, et al., Central Pressure More Strongly Relates to Vascular Disease and Outcome than Does Brachial Pressure, The Strong Heart Study, Hypertension 2007, 50:197-203.

Mase, et al., Feasibility of cuff-free measurement of systolic and diastolic arterial blood pressure, Journal of Electrocardiology 44 (2011) pp. 201-207.

Chen, et al., Continuous and Noninvasive Measurement of Systolic and Diastolic Blood Pressure by One Mathematical Model with the Same Model Parameters and Two Separate pulse Wave Velocities, Annals of Biomedical Engineering, vol. 40, No. 4, Apr. 2012, pp. 871-882.

Zheng, et al., Wearable Cuff-less PTT-based System for Overnight Blood Pressure Monitoring, 35th Annual International Conference of the IEEE EMBS, Osaka, Japan, Jul. 3-7, 2013, pp. 6013-6106.

Chobanian, et al., Seventh Report of the Joint National Committee on Prevention, Detection, Evaluation, and Treatment of High Blood Pressure, Hypertension, Dec. 2003, 42, pp. 1206-1252.

Mancia, et al., 2007 Guidelines for the management of arterial hypertension, European Heart Journal, 2007, 28, pp. 1462-1536.

International Search Report and Written Opinion dated Jun. 8, 2018 in co-pending PCT Application PCT/IB2018/051290.

Shih, et al.., Is Noninvasive Brachial Systolic Blood Pressure an Accurate Estimate of Central Aortic Systolic Blood Pressure?; American Journal of Hypertension, vol. 29, No. 11 (2015); pp. 1283-1291.

* cited by examiner

NON-INVASIVE BRACHIAL BLOOD PRESSURE MEASUREMENT

FIELD OF THE INVENTION

The invention pertains to measuring systolic and diastolic brachial blood pressure non-invasively using a cuff wrapped around a patient's upper arm. In particular, the invention is directed to recalibrating a brachial cuff volumetric displacement waveform so that its maximum and minimum values can be used to accurately estimate the value of the patient's brachial systolic and diastolic blood pressures as measured invasively, such as when using a catheter.

BACKGROUND OF THE INVENTION

Arterial blood pressure is a clinically important indicator of the status of the cardiovascular system, reflective of arterial and cardiac load and an early independent predictive marker of cardiovascular events and diseases. However, to measure the inter-arterial blood pressure accurately requires an invasive procedure to insert a catheter with a pressure sensor inside the artery. As a result, non-invasive methods were created to estimate pressure at the peripheral brachial artery.

One of the earliest non-invasive methods to estimate pressure in the brachial artery is the auscultatory method which requires inflating a cuff wrapped around the patient's upper arm and brachial artery until the brachial artery occludes (i.e., no blood flow). Then, the cuff is gradually deflated and blood starts flowing with "thumping" sounds that can be detected through a stethoscope. The first "thumping" sound should occur when the cuff pressure equals the patient's systolic pressure (maximum pressure during cardiac ejection) and the last "thumping" sound should occur when the cuff pressure equals the patient's diastolic pressure (minimum pressure during cardiac filling).

For decades, the auscultatory method was used for clinical hypertension diagnosis and had become the standard for non-invasive blood pressure measurement. However, the accuracy of the measured pressure value was dependent on the operator's acute detection of the heart sound and also dependent on the rate that the operator deflated the cuff. Because the accuracy of the auscultatory method is operator dependent, an automated method was established based on detecting oscillatory pulsations measured by the brachial cuff during cuff inflation or deflation. The height of the pulse oscillation increases when the cuff pressure decreases from systolic pressure to below systolic pressure and the height of the oscillation decreases when the cuff pressure decreases from above diastolic pressure to diastolic pressure and below. Based on this concept, current "oscillometric" devices apply different algorithms to detect oscillation heights related to systolic and diastolic pressure.

Oscillometric cuff devices are often called a non-invasive blood pressure devices or NIBP devices in the art. To be accepted for clinical use, an NIBP device has to show equivalence to the standard auscultatory method based on the American National Standard for Non-Invasive Automated Blood Pressure Devices, see, ANSI/AAMI/ISO 81060-2:2009, "Non-invasive sphygmomanometers—Part 2: Clinical validation of automated measurement type," Section 5.2.4.1.2 Part a—Criterion 1, page 20 (which states that the mean error for determination of all subjects in the test "shall not be greater than 5.0 mmHg with a standard deviation no greater than 8 mmHg.") Accordingly, any oscillometric cuff device can pass the validation requirements if the average difference with the auscultatory method for systolic and diastolic pressure is not more than 5 mmHg and the standard deviation is not more than 8 mmHg. This means that approved oscillometric devices can register a difference with the standard auscultatory method reaching above 20 mmHg for some data points.

Oscillometric automated blood pressure devices have been standard in clinical practice for many years, and have also been used in medical research to assess cardiovascular risk. Even though non-invasive blood pressure (NIBP) measurement identifies a percentage of the general population at risk of cardiovascular diseases, a large group is not identified by NIBP measurement to be at risk even though they may be at risk. The main reason is that measured blood pressure varies among different NIBP devices due to the different devices having different propriety algorithms for detecting systolic and diastolic pressure. Furthermore, when compared to invasive pressure values, NIBP devices have been shown to underestimate systolic pressure and overestimate diastolic pressure, see, Sharman et al, "Validation of non-invasive central blood pressure devices: Artery Society task force consensus statement on protocol standardization", *European Journal of Hypertension* 2017; Cloud et al, "Estimation of central aortic pressure by SphygmoCor® requires intra-arterial peripheral", *Clinical Science* (2003) 105, 219-225.Shoji et al, "Invasive validation of a novel brachial cuff-based oscillometric device (SphygmoCorXCEL) for measuring central blood pressure", *Journal of Hypertension* 2016, 34. Accordingly, since measuring brachial pressure invasively is the gold standard, non-invasive measurements that closer estimate the invasive pressure and overcome the errors inherent in cuff NIBP devices would be a significant improvement in the field of blood pressure measurement and its clinical importance.

SUMMARY OF THE INVENTION

The general purpose of the invention is to provide a non-invasive method of measuring brachial systolic and diastolic pressure that more accurately estimates its invasive equivalent, and consequently renders brachial systolic and diastolic measurements more clinically relevant. The invention applies linear and/or non-linear models to the cuff measured brachial pulse waveform based on the cardiovascular features of the arterial waveform. More specifically, the invention estimates brachial systolic and diastolic pressure values using a non-invasive cuff to measure initially non-invasive systolic and diastolic pressure and also measure a high fidelity brachial volumetric displacement waveform with it cardiovascular features preserved. Based on determined parameter values for one or more cardiovascular features of the waveform, it is recalibrated such that the maximum point of the curve provides an accurate estimate of the invasive brachial systolic pressure and the minimum point of the curve provides an accurate estimate of the invasive brachial diastolic pressure.

In one aspect of the invention, the invention pertains to a method of measuring a patient's brachial systolic and diastolic blood pressure non-invasively. As a first step, the method involves the use of a brachial cuff device having an inflatable brachial cuff, a tube, a pressure pump with a pressure control system and a pressure sensor that provides an analog signal of the pressure within the brachial cuff. The cuff is wrapped around the patient's upper arm and then the brachial cuff device is used in oscillometric mode to take initial non-invasive measurements of the patient's systolic blood pressure and diastolic blood pressure. These initial measurements are used to initially calibrate the patient's brachial volumetric displacement waveform. To measure the patient's brachial cuff volumetric displacement waveform, the brachial cuff is inflated to a constant pressure around the patient's upper arm. The brachial cuff is maintained at the constant pressure and the analog signal from the pressure sensor is recorded as the patient's brachial cuff volumetric waveform. The analog signal or its digital counterpart must be filtered through an appropriate band-pass filter, a combination of a low pass and high pass filter or another appropriate filter in order to produce a brachial cuff volumetric displacement waveform in which the cardiovascular features of the patient's waveform are preserved. Such a waveform is shown for example in FIG. 4. Importantly, the brachial cuff volumetric displacement waveform should have at least an identifiable first systolic peak, second systolic peak and incisura indicating the beginning of diastole. The specific filtering necessary for preserving the waveform features is dependent on the brachial cuff type and model. In the next step of the method, the recorded brachial cuff volumetric displacement waveform is initially calibrated using the patient's brachial systolic pressure and diastolic pressure as measured with the cuff in oscillometric mode. Using equation/equations based on linear and/or non-linear modeling, the calibrated cuff waveform is then transformed into a recalibrated waveform where its maximum and minimum correspond to the patient's invasive systolic and diastolic pressure respectively. Data shows that this method is capable of estimating the patient's systolic and diastolic brachial blood pressure within 3 mmHg of invasively measured systolic and diastolic pressures on a consistent basis.

In one exemplary embodiment of the invention, multiple recalibration equations are provided, and the selection of which recalibration equation to use is based on the detection or calculation of one or more parameters pertaining to the cardiovascular features of the initially-calibrated volumetric displacement waveform. The selection of the recalibration equation can be made using a decision tree, or with other algorithms that correlate waveform features to the appropriate recalibration equations, like support vector machines, linear and non-linear regression, neural networks and so on.

In accordance with one exemplary embodiment of the invention, five different recalibration equations are selected based on a decision tree. According to testing, two of the recalibration equations can apply if the augmentation index (AIx) is less than 28. In this case, one recalibration equation is used if the ejection duration (ED) is greater than or equal to 300 and another is used if the ejection duration (ED) is less than 300. If the augmentation index (AIx) is greater than or equal to 28 and the heart rate (HR) is less than 60, then a third recalibration equation is used. If the augmentation index (AIx) is greater than or equal to 28 and the heart rate (HR) is larger than 60, then a fourth recalibration equation is used if the ratio of the area under the curve during diastole ($AUC_d$) divided by the area under the curve during systole ($AUC_s$) is less than 100 and a fifth equation is used if that ratio is greater than or equal to 100. These values are illustrative, and will depend on the specific cuff device, the inflated pressure of the cuff when recording the initial waveform, and the mapping characteristics of the recalibration equations.

The form of the recalibration equations in the exemplary embodiment is a combination of linear and non-linear components, where the coefficients are selected so that the output from the recalibration equations provides an estimated waveform in which the maximum value matches data for invasively-measured brachial systolic pressure and the minimum of the outputted waveform matches data for the invasively-measured brachial diastolic pressure for each of the five identified situations. The inventor has discovered that a generalized linear transfer function is not capable of reliably and accurately mapping cuff measured NIBP to its invasive counterpart for the general population. The inventor has also discovered that it is best to determine the recalibration equations and the selection criteria for the specific NIBP device being recalibrated, for example by comparing non-invasive data measured with the device to simultaneously collected invasive data. In the exemplary embodiment of the invention, the form of the recalibration equations includes a non-linear component, such as a sigmoid function. Also, desirably, several sets of values for equation coefficients and constants are determined independently for the various recalibration equations in accordance with specific groups of data pertaining to the decision tree selection criteria. Machine learning techniques can be used to identify the decision tree criteria such that the recalibration equations for the respective groups of data result in reliably accurate recalibrated waveforms in which the maximum and minimum values are accurate estimates of invasively measured brachial systolic and diastolic pressure.

In another exemplary embodiment of the invention, a non-peripheral waveform other than a brachial cuff volumetric displacement waveform can be measured, calibrated and re-calibrated for use in the invention. For example, a non-invasive sensor can be used to record data representing the patient's raw peripheral waveform, such as using a tonometer to measure and record the patient's raw radial pressure waveform. The raw peripheral waveform can then be calibrated and recalibrated using a method similar to that used with the brachial cuff volumetric waveform. Typically, the form of the recalibration equations will be the same or similar to those used when a brachial cuff volumetric waveform is used but the coefficients and constants are likely to be different depending on the underlying data, and the parameters for the selecting the appropriate recalibration equation is also likely to be different depending on the underlying data.

In another aspect of the invention, the invention pertains to systems capable of implementing the methods described above. The system necessarily includes a brachial cuff device having a cuff, a pressure tube, a pressure control device, and a pressure sensor for outputting the raw analog signal, as well as analog or digital filters, and a digital signal processor or other computing means.

In another embodiment, through collected data, the NIBP-calibrated brachial cuff waveform (or other NIBP-calibrated peripheral waveform) with cardiovascular related features can be categorized based on the waveform features and expected invasive SP and DP using machine learning algorithms like support vector machine, random forest, k-nearest classification, or boosting. These algorithms will provide equations that separate the waveforms based on its features into categories where each category represents ISP and IDP range of values. Another embodiment using another machine learning method like neural network such that collected data can be used to train a neural network with waveform features as inputs and the invasive SP and DP. The advantage of these embodiments is that they do not require specific recalibration equations and use a single general method to estimate invasive SP and DP from the NIBP-calibrated brachial cuff waveform (or other NIBP-calibrated peripheral waveform) with cardiovascular related features.

Other features and advantages of the invention may be apparent to those skilled in the art upon reviewing the drawings and the following description thereof.

DETAILED DESCRIPTION

Figure 1:
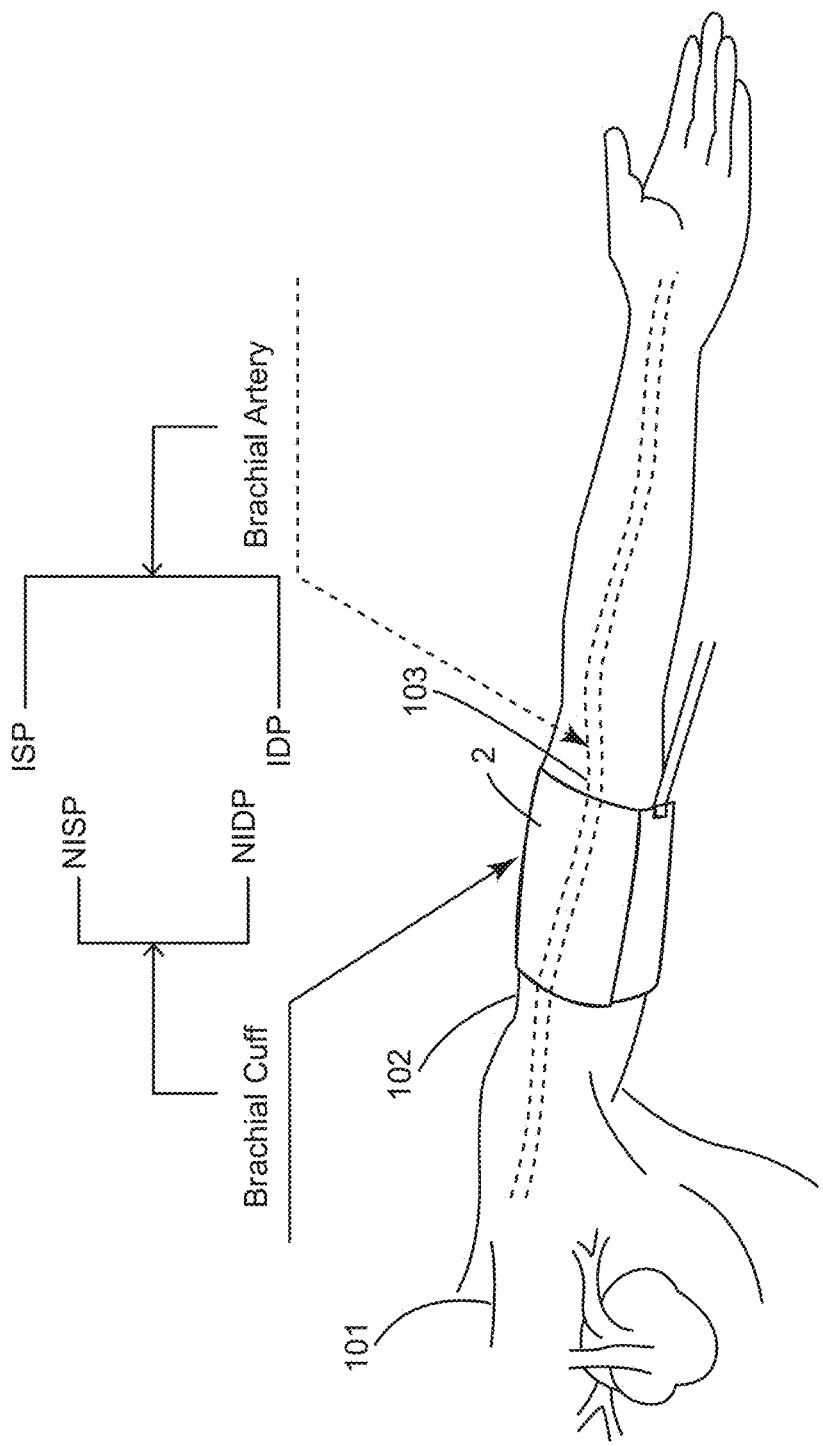
FIG. 1 illustrates the difference between non-invasive systolic and diastolic pressure (NISP/NIDP) measured by a brachial cuff-measured, and invasively measured systolic and diastolic pressure (ISP/IDP) in the brachial artery.

Referring to FIG. 1, as mentioned, there can be significant differences between invasive and non-invasive brachial arterial blood pressure values. FIG. 1 illustrates a brachial cuff 2 wrapped around the upper arm 102 of a patient 101 for the purpose of non-invasively measuring the patient's systolic and diastolic blood pressure in the brachial artery 103. The non-invasively measured systolic blood pressure is identified in FIG. 1 as NISP, and the non-invasively measured diastolic blood pressure is identified as NIDP. FIG. 1 also illustrates measuring the patient's systolic and diastolic pressures in the brachial artery 103 invasively (e.g., using a pressure sensor with a catheter inserted into the patient's arm 102 and brachial artery 103). The invasively measured systolic blood pressure is identified in FIG. 1 as ISP, and the invasively measured diastolic blood pressure is identified as IDP. As mentioned previously, invasively measured ISP and IDP are considered to be the gold standard for clinical and research analysis and present day inflated cuff, oscillometric systems typically underestimate systolic brachial pressure (i.e., NISP<ISP) and overestimate diastolic brachial pressure (i.e., NIDP>IDP). The aim of the current invention is to reduce or eliminate the difference prevalent between invasive measurements and non-invasive measurements.

Figure 2:
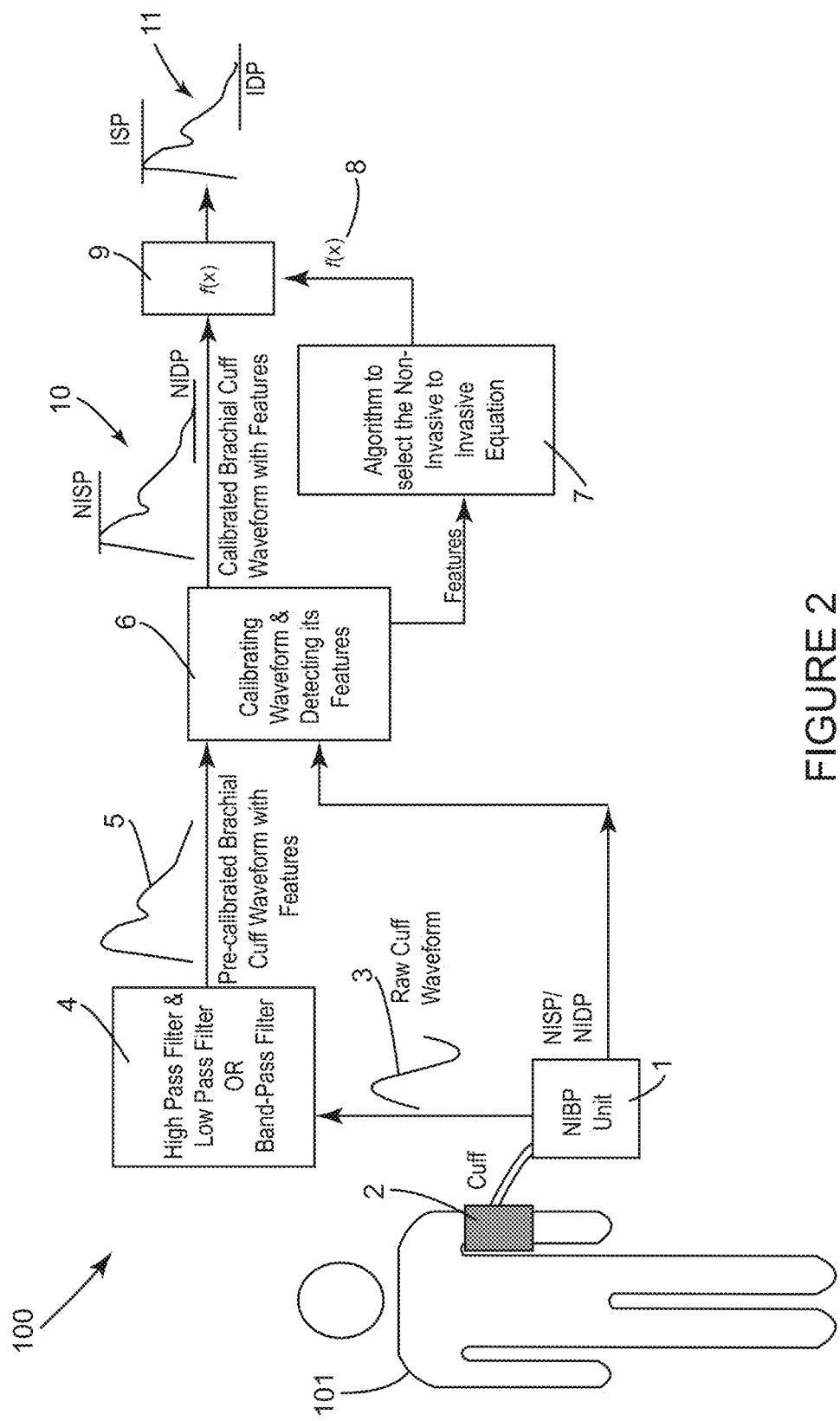
FIG. 2 is the schematic drawing illustrating implementation of the invention, which records a non-invasive brachial cuff volumetric displacement waveform, measures NISP and NIDP using a brachial cuff device and estimates ISP and IDP in the brachial artery after recalibration of the waveform.

FIG. 2 illustrates a system 100 configured in accordance with one exemplary embodiment of the invention. The system 100 in FIG. 2 includes a non-invasive blood pressure unit 1 (NIBP unit 1), the same as or similar to a conventional brachial cuff "oscillometric" blood pressure device. The NIBP unit 1 includes, e.g., a cuff 2, a pressure tube, an air pressure control, and a pressure sensor for sensing the pressure in the cuff 2 and outputting an analog signal. The NIBP unit 1 also includes control algorithms which operate in the oscillometric mode to determine NISP and NIDP, as is common in the art. With a cuff 2 wrapped around the patient's upper arm 102 (including the brachial artery 101), the NIBP unit 1 performs an oscillometric brachial blood pressure measurement resulting in a value for the non-invasive brachial systolic pressure (NISP) and non-invasive brachial diastolic pressure (NIDP). Then, while the cuff 2 is inflated at a constant pressure (below NIDP, between NIDP and NISP or above NISP), the NIBP unit 1 records a raw cuff waveform 3. The pressure of the inflated cuff will affect the shape of the recorded waveform, and therefore it is important that the cuff be inflated with respect to NISP and NIDP consistent with the inflation of the cuff for the data collected to determine the recalibration equations discussed below. For example, if the recalibration equations are determined based on data collected with the cuff inflated below NIDP for the test population, then the raw waveform 3 should be collected with the cuff inflated below the patient's NIDP. In this embodiment, it is preferred that the inflated cuff pressure have a 10% difference or more compared the patient's DP in order to avoid borderline effects. The same considerations apply with respect to both DP and SP in the case that the recalibration equations are determined based on data collected with the cuff inflated between NIDP and NISP for the test population, or with respect to SP in the case that the recalibration equations are determined based on data collected with the cuff inflated above NISP for the test population. In some applications, it may be necessary to maintain the pressure of the inflated cuff between NIDP and NISP in order to ensure sufficient resolution of the captured waveform.

The raw cuff waveform 3 is processed through a high pass filter and low pass filter or a band pass filter 4 to produce a pre-calibrated brachial cuff waveform with cardiovascular related features 5 preserved. This waveform 5 is brachial cuff volumetric displacement waveform, which contains and preserves the cardiovascular features present in the patient's brachial artery pressure waveform, however, the amplitude of the waveform 5 needs to be calibrated. While the filtering of the raw cuff waveform 3 is dependent on the particular cuff device, the cuff pressure relative to NISP or NIDP and NIBP unit 1 used, the filtering in an exemplary embodiment uses a low pass filter with cutoff frequency between 30 to 40 Hz, and high pass filter with pass frequency between 0.7 to 1 Hz has been found suitable to capture a raw waveform in which the cardiovascular features, including the foot, first systolic peak, second systolic peak and incisura, are preserved in the data. The purpose of the low pass filter is to preserve volume, pressure or flow signal frequencies that are related to physiological function and eliminate noises related to environmental inferences such as power sources noise. The choice of the low pass cutoff frequency is based on the fact that all physiological features in a pressure, volume, flow waveforms are within 25 Hz of the signal spectrum (See FIG. 26.21 in W. Nichols and M. O'Rourke, "McDonald's Blood Flow in Arteries: Theoretical, Experimental and Clinical Principles," $5^{th}$ Edition). The purpose of the high pass filter is to eliminate low frequencies related to artifacts noise as a result of arm movements, breathing effect or the tube and cuff reaction to the compliance to pressure. These low frequency artifacts, which cause signal baseline drift and can dampen signal shape, are usually below 1 Hz, hence the high pass filter pass frequency. Both filters, which can be implemented as a Chebyshev type filters with pass band ripple or stop band ripple of −3 dB, can be combined into one band pass filter where it pass all frequencies between 0.7 to 40 Hz.

The operations after the NIBP unit 1 in FIG. 2 are preferably implemented in a digital signal processor, or other computing device. However, the electronic filters discussed in connection with block 4 can be analog or digital, with analog-to-digital conversion occurring after block 4 or prior to block 4, respectively.

Block 6 in FIG. 2 depicts both the pre-calibrated waveform 5 (with features preserved) and the NISP and NIDP values being entered into an algorithm (e.g. software code) that calibrates the pre-calibrated brachial cuff waveform 5 so that the maximum and minimum values of waveform 5 are equivalent to NISP and NIDP, respectively. This initial calibration results in a NIBP-calibrated brachial cuff waveform with preserved features as indicated by reference number 10 in FIG. 2. In accordance with the invention, it is possible to calibrate the pre-calibrated brachial cuff waveform 5 using a mean pressure (NIMP), such as calibrating with NIDP and NIMP. Under these circumstances, the calibrated waveform 5 shall be considered a NIBP-calibrated waveform 5. If this is the case, then the same calibration should occur when establishing the recalibration equations as explained in connection with FIG. 3." In addition, the software depicted in block 6 also determines parameter values for cardiovascular related features of the NISP/NIDP calibrated brachial cuff waveform 10. The specific cardiovascular features used in this exemplary embodiment are explained in connection with FIG. 4.

Figure 3:
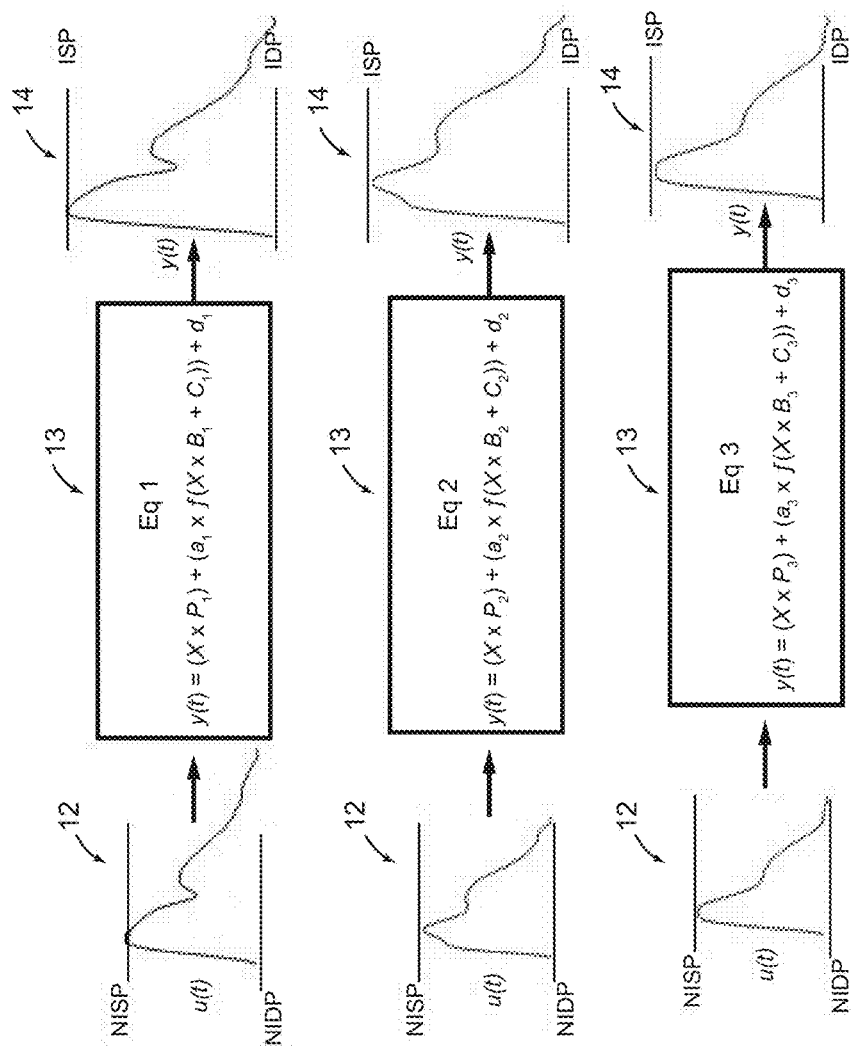
FIG. 3 shows an exemplary form of non-invasive to invasive blood pressure waveform recalibration equations for brachial pulse waveforms having different waveform shapes.
Figure 5:
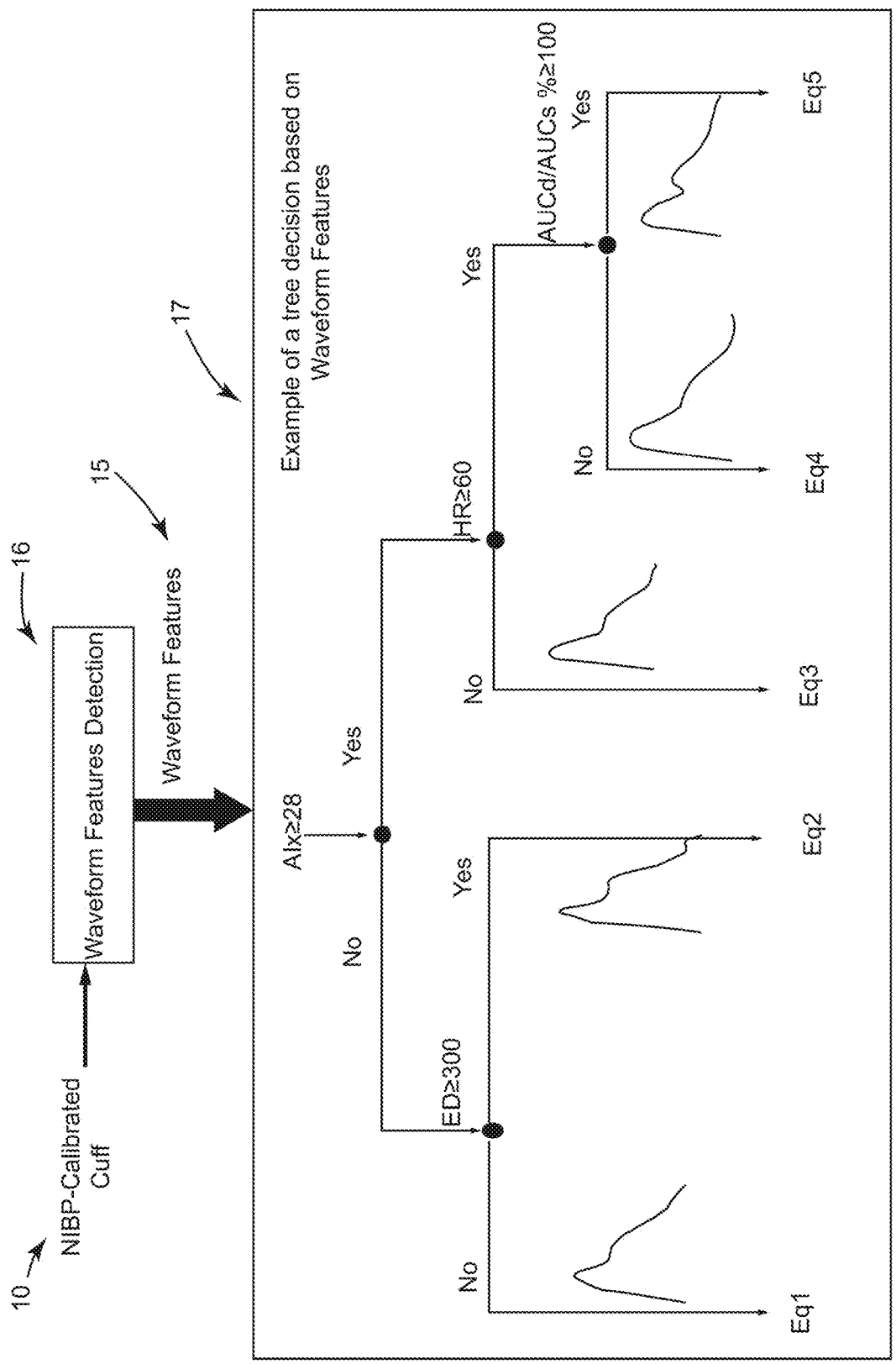
FIG. 5 shows an example decision tree based on the initially calibrated (NISP/NIDP) brachial cuff pulse waveform features that determine which non-invasive to invasive blood pressure recalibration equation should be used.

Referring still to FIG. 2, the determined feature parameter values from block 6 are the input for a selection algorithm, block 7, that determines which recalibration equation $f_i(x)$, reference number 8, should be used to recalibrate the NIBP/NISP calibrated waveform 10 in terms of invasive brachial blood pressure instead of non-invasive brachial blood pressure. Examples of a selection algorithm 7 and recalibration equations 8 are shown in FIG. 5 and FIG. 3 respectively, and are discussed in more detail below. Block 9 in FIG. 2 indicates that the selected recalibration equation 8 operates on the initially calibrated (NIDP/NISP) brachial cuff waveform 10, to produce a recalibrated waveform 11 where the maximum and the minimum values provide accurate estimates of the invasive brachial systolic (ISP) and diastolic pressure (IDP), respectively.

Data of invasive brachial arterial blood pressure alongside brachial cuff NIBP measurements, which provide NISP and NIDP, were used to calculate the non-invasive to invasive blood pressure recalibration equations 8. More specifically, data was collected from 150 patients with wide range of brachial SP, DP (SP range from 88 to 216 mmHg and DP range from 40 to 93 mmHg) and heart rate (from 41 to 102 beats per minute) providing a representation of the general population. The collected data included invasively measured brachial pressure waveform data (through fluid filled catheter with properly tested frequency response for every measurement) and contemporaneously collected NIBP measured SP and DP, and filtered NIBP brachial waveform data. The cuff was inflated at 10% of the patient's NIDP to collect the filtered NIBP brachial waveforms. Referring to FIG. 3, a method of system identification was used to establish the coefficients for proposed recalibration equations 13 as shown in FIG. 3. In the exemplary embodiment, a non-linear sigmoid function system identification method, which constitutes linear and non-linear components. In general, the non-invasively collected data 12 is filtered (like block 4) and NIBP calibrated (like block 6) to represent the NIBP calibrated brachial cuff waveform and is the input for the proposed recalibration equations 13. Invasively collected data 14 for the brachial artery, necessarily having its maximum and minimum values equal to ISP and IDP, respectively, is the output of the proposed recalibration equations 13. Given the known input 12 and output 14 from the collected data, recalibration equations 13 with unknown coefficients are proposed. Then, the coefficients are estimated such that the difference between the equation output and the data collected for the invasive blood pressure measurements is minimized. The recalibration equations can theoretically be linear or non-linear or combination of both types, however, it has been found that using a non-linear component produces more accurate results. In the exemplary embodiment of the invention, the proposed form has linear and non-linear components and can be expressed as follow:

$$y(t)=(X \times P_i)+(a_i \times f(X \times B_i+C_i))+d_i \quad [1]$$

where y(t) is the output waveform at time t $P_i, B_i, C_i$ are matrices of coefficients for each recalibration equation i, and $a_i, d_i$ are scalars (constants) for each recalibration equation i.

Further, vector X in equation [1] is a vector of delayed input and output values which can be represented as follow:

$$X=[u(t)u(t-1) \ldots u(t-na)y(t-1) \ldots y(t-nb)] \quad [2]$$

where u(t) is the input waveform at time t, u(u−1) is the input waveform at time t−1, u(t−na) is the input waveform at time t−na, y(t−1) is the output waveform at time t−1, y(t−nb) is the input waveform at time t−nb, and na, nb are the number of delay points for the input and output signals respectively.

In equation [1], f( ) is a non-linear function which in this example is a sigmoid function expressed as follow:

$$f(z) = \frac{1}{e^{-z}+1}$$

To illustrate how the equation works, assume that na and nb are equal to 1, then vector X in equation [1] will be $$X=[u(t)u(t-1)y(t-1)] \quad [3]$$

Accordingly, $$P_i = \begin{bmatrix} p_1 \\ p_2 \\ p_3 \end{bmatrix} \quad [4]$$

$$B_i = \begin{bmatrix} b_{1,1} & b_{2,1} & b_{3,1} \\ b_{2,1} & b_{2,2} & b_{2,3} \\ b_{3,1} & b_{3,2} & b_{3,3} \end{bmatrix} \quad [5]$$

$$C_i = [c_1 \ c_2 \ c_3] \quad [6]$$

Then, substituting equations [3] to [6] into equation [1], the result will be $$y(t) = \left([u(t) \ u(t-1) \ y(t-1)] \times \begin{bmatrix} p_1 \\ p_2 \\ p_3 \end{bmatrix}\right) + \\ \left(a_i \times f\left([u(t) \ u(t-1) \ y(t-1)] \times \begin{bmatrix} b_{1,1} & b_{2,1} & b_{3,1} \\ b_{2,1} & b_{2,2} & b_{2,3} \\ b_{3,1} & b_{3,2} & b_{3,3} \end{bmatrix}\right)\right. \\ \left.[c_1 \ c_2 \ c_3]\right) + d_i \quad [7]$$

The goal of the system identification method is to estimate coefficient matrices $P_i$, $B_i$, $C_i$, and the constants $a_i$, $d_i$ to minimize the difference between estimated output and the collected invasive data 14.

Applying the system identification method on invasive data collected for a sampling of the general population in the exemplary embodiment resulted in five (5) different recalibration equations 8 (see, FIG. 2) that can be implemented on the general population. In other words, the final form of the proposed recalibration equations 13 in FIG. 3 corresponds to the recalibration equations 8 programmed in to the system 100, and used in practice to detect brachial SP and DP using a brachial cuff. The final form of the proposed recalibration equations 13 is determined for different groupings of input 12 and output 14 waveform data, in which the groupings are based on waveform feature parameters determined by applying the system identification method. In the exemplary embodiment, the selection algorithm 7 is a decision tree, see FIG. 2, that determines which recalibration equation 8 should be used based on waveform features.

Figure 4:
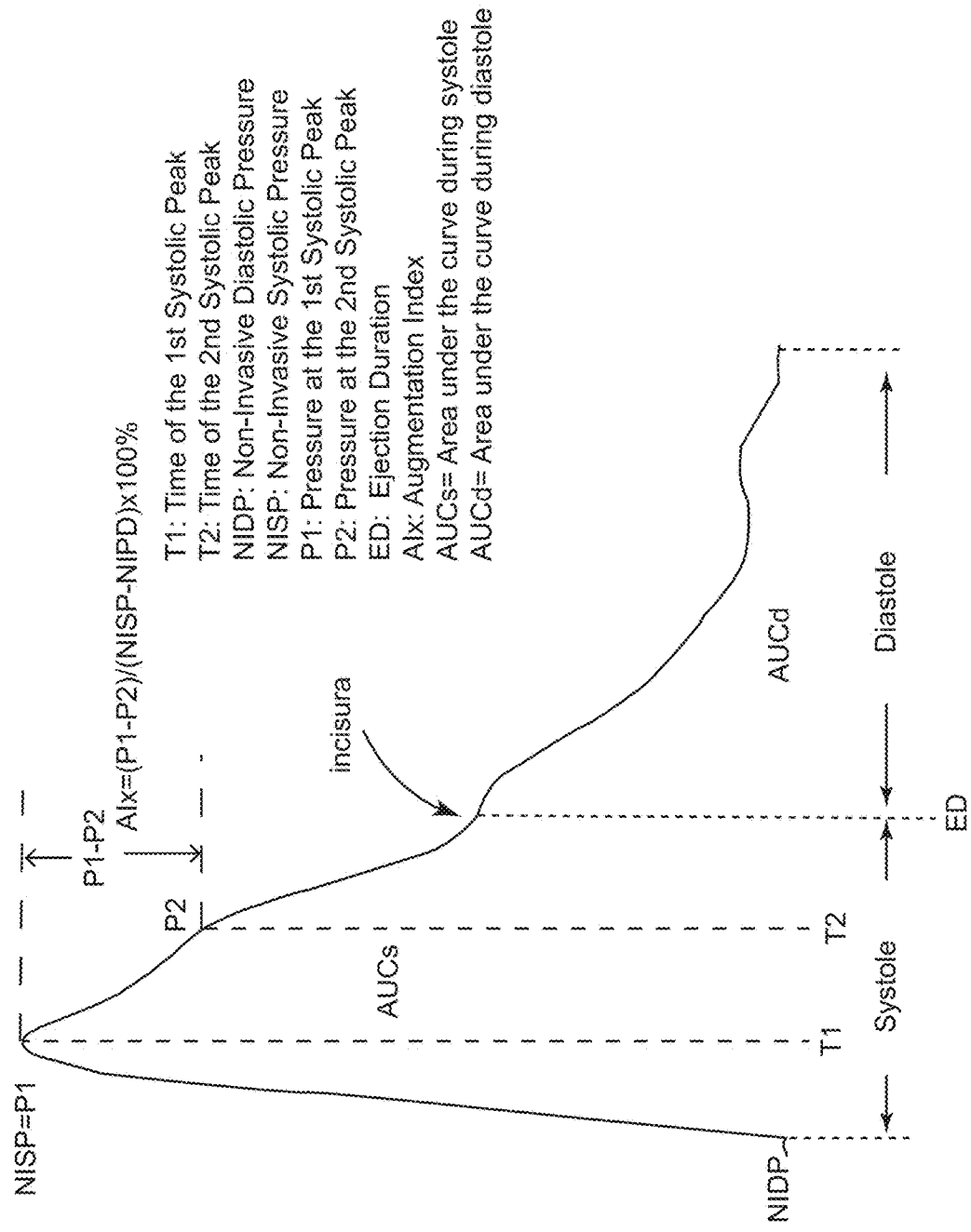
FIG. 4 shows and defines certain cardiovascular features of an initially calibrated (NISP/NIDP) brachial cuff volumetric displacement waveform.

FIG. 4 describes some of the brachial waveform cardiovascular related features, which are used as inputs to the selection algorithm 7 in this exemplary embodiment. The cardiovascular related features and others can be detected or calculated, e.g., using the through derivative method as described in U.S. Pat. No. 5,265,011 to Michael O'Rourke, entitled "Method for ascertaining the pressure pulse and related parameters in the ascending aorta from the contour of the pressure pulse in the peripheral arteries", which is herby incorporated by reference herein, or other suitable mathematical method in time or frequency like wavelet analysis. Exemplary features that can be used by the selection algorithm include, for example, NISP, NIDP, AIx, AUCs/AUCd, P1, P2, T1, T2, and ED as described in FIG. 4. Other features like mean pressure, heart rate, cardiac period and slope of the systolic upstroke, which also can be detected from the NIBP calibrated waveform, can also be used as input to the algorithm.

The parameters and threshold values for the parameters in order to construct the decision tree selection algorithm 7, which selects the appropriate recalibration equation 8 to recalibrate from NISP/NIDP to ISP/IDP based on the recorded NIBP-calibrated waveform characteristics, can be determined by training decision tree algorithm to determine the threshold and structure of the tree. However, the recalibration equations and selection algorithm, or other suitable algorithm for recalibration conversion, can be developed using other types of machine learning such as support vector machine, linear and nonlinear regression, and neural network. In any event, the overall purpose is to provide an algorithm in which data representing a NIBP-calibrated cuff waveform with cardiovascular features preserved serve as the input, and the maximum and minimum value of the output waveform closely estimates ISP and IDP, respectively, based on known population data.

FIG. 5 illustrates the operation of the selection algorithm 7. The selection algorithms 7 developed to date, based on testing and analysis, are somewhat more complicated than the algorithm shown in FIG. 5. The illustrative selection algorithm in FIG. 5 is in the form of a decision tree that is used to determine the appropriate recalibration equation 8 (NISP/NIDP to ISP/IDP) based on the detected or calculated waveform features or parameters. The recalibration equations 8 are labelled Eq1, Eq2, Eq3, Eq4 and Eq5 in FIG. 5. Block 16 in FIG. 5 depicts pulse waveform features 15 being detected from the NIBP-calibrated cuff waveform 10. As mentioned, suitable feature detection methods include the derivative method or other mathematical methods in time or frequency domain. The values detected or calculated pertaining to the waveform features 15 are the input to the decision tree 17, which in this example serves as the selection algorithm 7 in FIG. 2. The decision tree 17 decides which recalibration equation Eq1, Eq2, Eq3, Eq4 or Eq5 to use according to the values of the detected or calculated waveform features. For purposes of illustration, in FIG. 5, one of five NISP/NIDP to ISP/IDP recalibration equations (Eq1, Eq2, Eq3, Eq4 or Eq5) can be selected based on values of AIx, ED, heart rate (HR) and the percentage ratio of AUCd to AUCs. As mentioned, the waveform parameter values for the decision tree 17 and the threshold values for the decision tree 17 are based on testing and data analysis and are disclosed for purposes of illustration. Other examples may use more waveform features with more branches in the decision tree. Also, other algorithms that correlate the waveform features with the appropriate NISP/NIDP to ISP/IDP recalibration equation like support vector machine, linear and nonlinear regression, and neural network can also be used as the selection algorithm.

Those skilled in the art will appreciate that it is most desirable to develop the recalibration and selection algorithms for a specific cuff device and NIBP unit. However, the algorithms developed for use one cuff device and NIBP unit are likely to improve the accuracy of the detected SP and DP for another cuff device and NIBP unit to the extent different models have similar characteristics.

Results: Using a subset of the collected data to train a decision tree where the inputs are waveform features and the outputs were the recalibration equations (Eq1, Eq2, Eq3, Eq4 and Eq5). The decision tree showed, for example that if AIx is less than 28, NIDP less than 77, ED less than 330 and AIx is larger than or equal to 14 then Eq1 is chosen as the recalibration equation. If AIx is less than 28, NIDP less than 77, ED less than 330 and AIx is less than 14 then Eq2 is chosen as the recalibration equation. If AIx is greater than or equal to 28, NIDP greater than or equal to 85, the percentage ratio of AUCd to AUCs is greater than or equal to 100, HR less than 60 and ED is greater than or equal to 300 then Eq3 is chosen as the recalibration equation. If AIx is greater than or equal to 28, NIDP greater than or equal to 85, HR larger than or equal 60, and the percentage ratio of AUCd to AUCs is less than 100, then Eq4 is chosen as the recalibration equation. If AIx is greater than or equal to 28, NIDP greater than or equal to 85, HR larger than or equal 60, and the percentage ratio of AUCd to AUCs is greater than or equal to 100, then Eq5 is chosen as the recalibration equation.

Figure 6A:
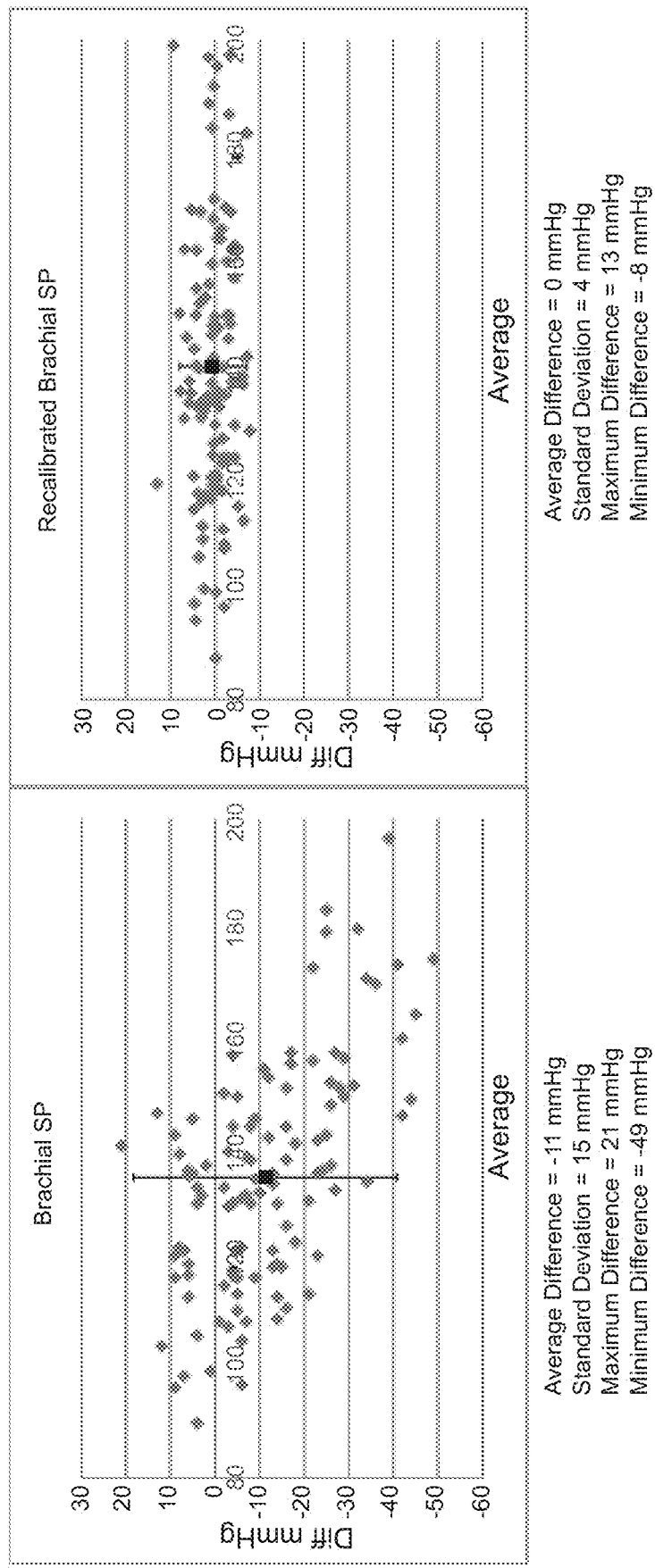
FIG. 6A left plot is a plot of the average of versus the difference between NIBP and invasive brachial systolic pressure (SP). Right plot is a plot of the average of versus the difference between recalibrated and invasive brachial SP. The left text box shows the average, standard deviation, the maximum and the minimum difference between NIBP and invasive brachial SP. The right text box shows the average, standard deviation, the maximum and the minimum difference between recalibrated and invasive brachial SP.

When applying the determined decision tree on the tested data (N=110), the results and the plots are shown in FIG. 6. The graph on the left in FIG. 6A shows the plot of the average of versus the difference between NIBP and invasive brachial systolic pressure (SP). After applying the recalibration equation as determined by the decision tree and based on the waveform features, the graph on the right in FIG. 6A shows large, significant reductions in the difference between the recalibrated and the invasive brachial SP—illustrating the accuracy of the recalibration. The average and standard deviation of the difference were reduced significantly from −11±15 mmHg to 0±4 mmHg.

Figure 6B:
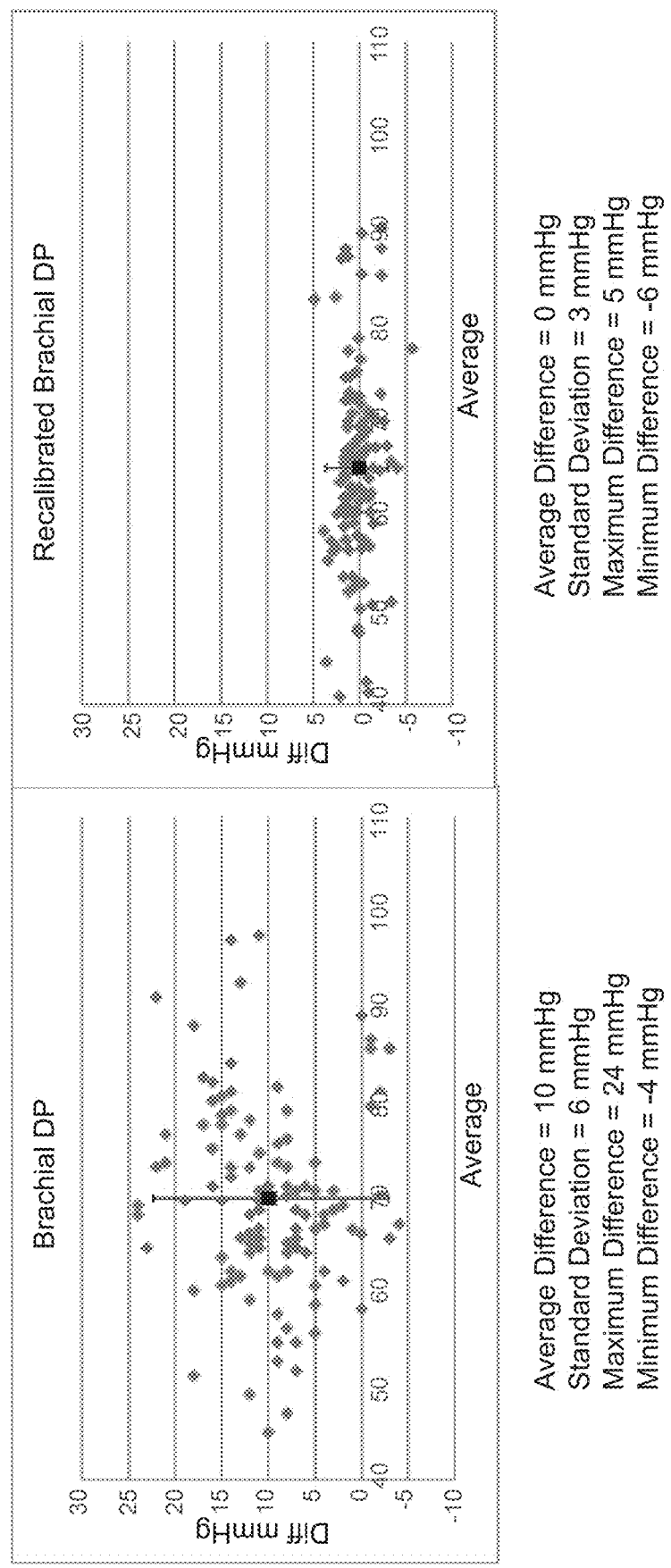
FIG. 6B left plot is a plot of the average of versus the difference between NIBP and invasive brachial diastolic pressure (DP). Right plot is a plot of the average of versus the difference between recalibrated and invasive brachial DP. The left text box shows the average, standard deviation, the maximum and the minimum difference between NIBP and invasive brachial DP. The right text box shows the average, standard deviation, the maximum and the minimum difference between recalibrated and invasive brachial DP.

The graph on the left in FIG. 6B shows the plot of the average of versus the difference between NIBP and invasive brachial diastolic pressure (DP). After applying the recalibration equation as determined by the decision tree and based on the waveform features, the graph on the right in FIG. 6B shows large, significant reductions in the difference between the recalibrated and the invasive brachial DP illustrating the accuracy of the recalibration. The average and standard deviation of the difference were reduced significantly from 10±6 mmHg to 0±3 mmHg.

Depending on the sophistication of the mathematical model, it may be possible in accordance with the invention to develop a single recalibration equation or set of equations that accounts for waveform features and recalibrates the NIBP-calibrated cuff waveform to obtain maximum and minimum values corresponding to brachial ISP and IDP.

In another embodiment, through collected data, the NIBP-calibrated brachial cuff waveform with cardiovascular related features can be categorized based on the waveform features and expected invasive SP and DP using machine learning algorithms like support vector machine, random forest, k-nearest classification, or boosting. These algorithms will provide equations that separate the waveforms based on its features into categories where each category represents ISP and IDP range of values. Another embodiment using another machine learning method like neural network such that collected data can be used to train a neural network with waveform features as inputs and the invasive SP and DP. The advantage of these embodiments that they do not require specific recalibration equations and use a single general method to estimate invasive SP and DP from the NIBP-calibrated brachial cuff waveform with cardiovascular related features.

Figure 7:
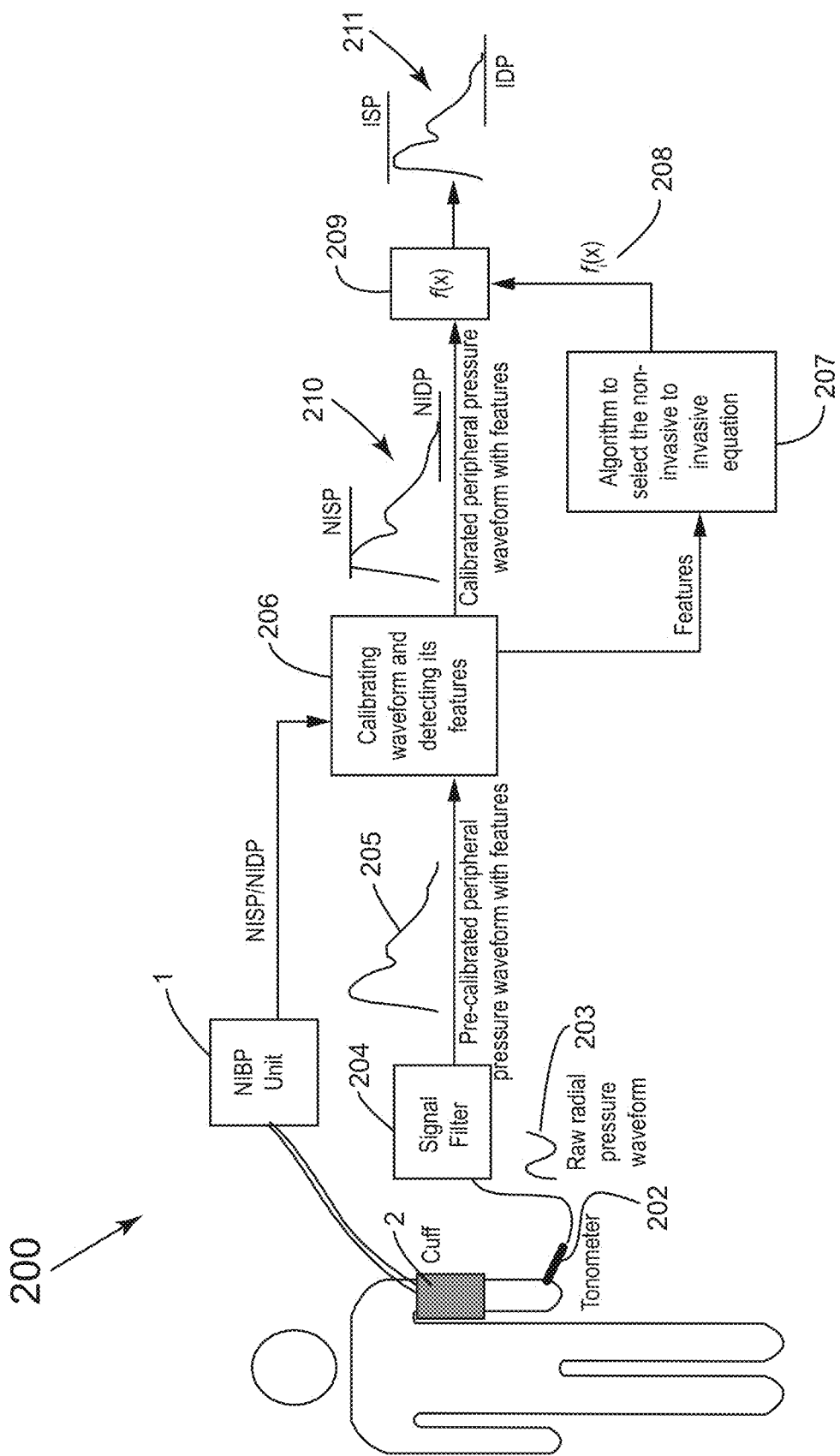
FIG. 7 is the schematic drawing illustrating implementation of another embodiment of the invention, which records a non-invasive radial pressure waveform with a tonometer, measures NISP and NIDP using a brachial cuff device and estimates ISP and IDP in the brachial artery after recalibration of the non-invasive radial pressure waveform.

FIG. 7 illustrates a system 200 configured in accordance with another exemplary embodiment of the invention. This system 200 is similar to system 100 shown in FIG. 2 except it uses a tonometer 202 to measure a raw radial pressure waveform 203, rather than the cuff to measure a raw cuff waveform. Similar reference numbers are used in FIG. 7 as in FIG. 2 to represent similar components. The system 200 in FIG. 7 includes a non-invasive blood pressure unit 1 (NIBP unit 1), which is the same as or similar to a conventional brachial cuff "oscillometric" blood pressure device. The NIBP unit 1 includes, e.g., a cuff 2, a pressure tube, an air pressure control, and a pressure sensor for sensing the pressure in the cuff 2. The NIBP unit 1 also includes control algorithms which operate in the oscillometric mode to determine NISP and NIDP, as is common in the art. With a cuff 2 wrapped around the patient's upper arm (including the brachial artery), the NIBP unit 1 performs an oscillometric brachial blood pressure measurement resulting in a value for the non-invasive brachial systolic pressure (NISP) and non-invasive brachial diastolic pressure (NIDP). Then, the tonometer 202 is used to capture the raw waveform 203. Other sensors can be used to collect the raw peripheral waveform as well, such as an optical sensor. The raw peripheral waveform 203 is processed through a high pass filter and low pass filter or a band pass filter 204 to remove low and high frequency noise and produce a pre-calibrated peripheral waveform with cardiovascular related features 205 preserved. This waveform 205 contains and preserves the cardiovascular features present in the patient's peripheral pressure waveform, however, the amplitude of the waveform 205 needs to be calibrated.

The operations after the NIBP unit 1 in FIG. 7 are preferably implemented in a digital signal processor, or other computing device. However, the electronic filters discussed in connection with block 204 can be analog or digital, with analog-to-digital conversion occurring after block 204 or prior to block 204, respectively.

Block 206 in FIG. 7 depicts both the pre-calibrated waveform 205 (with features preserved) and the NISP and NIDP values being entered into an algorithm (e.g. software code) that calibrates the pre-calibrated peripheral pressure waveform 205 so that the maximum and minimum values of waveform 205 are equivalent to NISP and NIDP, respectively. This initial calibration results in a NIBP-calibrated peripheral pressure waveform with preserved features as indicated by reference number 210 in FIG. 7. In accordance with the invention, it is possible to calibrate the pre-calibrated waveform 205 using a mean pressure (NIMP), such as calibrating with NIDP and NIMP. Under these circumstances, the calibrated waveform 205 shall be considered a MBP-calibrated waveform 205. If this is the case, then the same calibration should occur when establishing the recalibration equations as explained in connection with FIG. 3. In addition, the software depicted in block 206 also determines parameter values for cardiovascular related features of the NISP/NIDP calibrated peripheral pressure waveform 210. Cardiovascular features used in this exemplary embodiment are the same as explained in connection with FIG. 4.

Referring still to FIG. 7, the determined feature parameter values from block 206 are the input for a selection algorithm, block 207, that determines which recalibration equation $f_i(x)$, reference number 208, should be used to recalibrate the NIBP/NISP calibrated waveform 210 in terms of invasive brachial blood pressure instead of non-invasive brachial blood pressure. The selection algorithm 207 and recalibration equations 208 may take the form described in FIGS. 3 and 5, although the coefficients and constant values for the recalibration equations and the selection criteria need to be fitted to data for the peripheral pressure waveform, instead of the cuff waveform. Block 209 in FIG. 7 indicates that the selected recalibration equation 208 operates on the initially calibrated (NIDP/NISP peripheral pressure waveform 210, to produce a recalibrated waveform 211 where the maximum and the minimum values provide accurate estimates of the invasive brachial systolic (ISP) and diastolic pressure (IDP), respectively.

In the foregoing description, certain terms have been used for brevity, clarity, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims. Each limitation in the appended claims is intended to invoke interpretation under 35 U.S.C. § 112, sixth paragraph, only if the terms "means for" or "step for" are explicitly recited in the respective limitation.

What is claimed is:

1. A method of measuring a patient's invasively equivalent systolic and diastolic brachial blood pressure non-invasively comprising the steps of:
providing a brachial cuff device with an inflatable cuff, a tube, a pressure pump with a pressure control system, and a pressure sensor to measure the pressure in the inflatable cuff;
using the brachial cuff device in oscillometric mode with the inflatable cuff wrapped around the patient's upper arm to take measurements of the patient's systolic blood pressure and diastolic blood pressure;
inflating the inflatable cuff around the patient's upper arm to a constant pressure and maintaining the inflatable cuff at said constant pressure while recording data representing the patient's raw brachial cuff volumetric displacement waveform;
filtering the data representing the patient's raw brachial cuff volumetric displacement waveform through a low pass filter and a high pass filter to obtain data representing a pre-calibrated brachial cuff volumetric displacement waveform in which the patient's cardiovascular waveform features are preserved;
using the measurements of the patient's systolic blood pressure and diastolic blood pressure as measured with the brachial cuff device in oscillometric mode to calibrate the pre-calibrated brachial cuff volumetric displacement waveform resulting in a NIBP-calibrated brachial cuff volumetric displacement waveform;
determining values for one or more parameters pertaining to cardiovascular features of the NIBP-calibrated brachial cuff volumetric displacement waveform;
providing multiple recalibration equations, wherein said multiple recalibration equations are determined by comparing groupings of data collected from a general population correlating NIBP-calibrated brachial cuff waveform data to invasively measured brachial pressure waveform data, wherein said groupings of data are grouped according to values for one or more parameters pertaining to cardiovascular features of the NIBP-calibrated cuff waveform data from the general population, and said collected data from the general population comprises at least waveform data measured with the specific type of brachial cuff device that is being recalibrated, brachial systolic and diastolic blood pressure values measured in oscillometric mode using the specific type of brachial cuff that is being recalibrated, and invasively measured brachial systolic and diastolic blood pressure values;
selecting one of the multiple recalibration equations based on the determined values for the one or more parameters pertaining to the cardiovascular features of the MBP-calibrated volumetric displacement waveform;
recalibrating the NIBP-calibrated brachial cuff volumetric displacement waveform using the selected recalibration equation to produce a recalibrated brachial cuff volumetric displacement waveform; and
estimating a value for the patient's invasively equivalent brachial systolic blood pressure as a maximum value of the recalibrated brachial cuff volumetric displacement waveform and estimating a value for the patient's invasively equivalent brachial diastolic blood pressure as a minimum value of the recalibrated brachial cuff volumetric displacement waveform.

2. The method as recited in claim 1 wherein the one or more parameters pertaining to the cardiovascular features of the NIBP-calibrated volumetric displacement waveform comprise multiple parameters and the multiple parameters include augmentation index, ejection duration, heartrate, and a ratio of area under the MBP-calibrated volumetric displacement waveform during diastole divided by the area under the NIBP-calibrated volumetric displacement waveform during systole.

3. The method as recited in claim 1 wherein the selected recalibration equation is selected using a decision tree based on the determined values for the one or more parameters pertaining to the cardiovascular features of the NIBP-calibrated volumetric displacement waveform.

4. The method as recited in claim 3 wherein the one or more parameters pertaining to cardiovascular features of the NIBP-calibrated volumetric displacement waveform comprise multiple parameters and the multiple parameters include augmentation index (AIx), ejection duration (ED), heart rate (HR), and a ratio of the area under the NIBP-calibrated volumetric displacement waveform during diastole ($AUC_d$) divided by the area under the NIBP-calibrated volumetric displacement waveform during systole ($AUC_s$).

5. The method as recited in claim 4 wherein a first recalibration equation is selected if the augmentation index (AIx) is less than an AIx threshold value and the ejection duration (ED) is less than an ED threshold value, a second recalibration equation is selected if the augmentation index (AIx) is less than an AIx threshold value and the ejection duration (ED) is greater than or equal to an ED threshold value, a third recalibration equation is selected if the augmentation index (AIx) is greater than or equal to an AIx threshold value and the heart rate (HR) is less than an HR threshold value, a fourth recalibration equation is selected if the augmentation index (AIx) is greater than or equal to an AIx threshold value and the heart rate (HR) is greater than or equal to an HR threshold value and the ratio of the area under the curve during diastole ($AUC_d$) divided by the area under the curve during systole ($AUC_s$) is less than an AUC threshold value, and a fifth recalibration equation is selected if the augmentation index (AIx) is greater than or equal to an AIx threshold value and the heart rate (HR) is greater than or equal to an HR threshold value and the ratio of the area under the curve during diastole ($AUC_d$) divided by the area under the curve during systole ($AUC_s$) is greater than or equal to an AUC threshold value.

6. The method as recited in claim 1 wherein the multiple recalibration equations include a combination of linear components and non-linear components.

7. The method as recited in claim 6 wherein each of the multiple recalibration equations has the following form:

$$y(t) = ([u(t)\,u(t-1) \ldots u(t-na)\,y(t-1) \ldots y(t-nb)] \times P_i) + \\ (a_i \times f([u(t)\,u(t-1) \ldots u(t-na)\,y(t-1) \ldots y(t-nb)] \times B_i + C_i)) + d_i$$

where y(t) is an output recalibrated waveform at time t $P_i$, is na+nb+1 by 1 matrix of coefficients for recalibration equation i $B_i$, is na+nb+1 by na+nb+1 square matrix of coefficients for recalibration equation i $C_i$, is na+nb+1 by 1 matrix of coefficients for recalibration equation i na, nb are a number of delay points for input and output signals respectively, $a_i$, $d_1$ are scalars (constants) for recalibration equation i u(t) is the input NIBP calibrated waveform at time t, u(t−1) is the input NIBP calibrated waveform at time t−1, u(t−na) is the input NIBP calibrated waveform at time t−na, y(t−1) is the output recalibrated waveform at time t−1, y(t−nb) is the input recalibrated waveform at time t−nb, and and f( ) is a non-linear sigmoid function expressed as follows:

$$f(z) = \frac{1}{e^{-z}+1}$$

where (z)=([u(t) u(t−1) u(t−na) y(t−1) . . . y(t−nb)]×$B_i$+ $C_i$).

8. The method as recited in claim 1 wherein the constant pressure to which the inflatable cuff is inflated around the patient's upper arm while recording data representing the patient's raw brachial cuff volumetric displacement waveform is at or above the patient's diastolic blood pressure as measured by the brachial cuff device in the oscillometric mode.

9. The method as recited in claim 1 wherein the constant pressure to which the inflatable cuff is inflated around the patient's upper arm while recording data representing the patient's raw brachial cuff volumetric displacement waveform is at or below the patient's diastolic blood pressure as measured by the brachial cuff device in the oscillometric mode.

10. A method of measuring a patient's invasively equivalent systolic and diastolic brachial blood pressure non-invasively comprising the steps of:
    providing a brachial cuff device with an inflatable cuff, a tube, a pressure pump with a pressure control system, and a pressure sensor to measure the pressure in the inflatable cuff;
    using the brachial cuff device in oscillometric mode with the inflatable cuff wrapped around the patient's upper arm to take measurements of the patient's systolic blood pressure and diastolic blood pressure;
    recording data representing a peripheral, non-invasive waveform of the patient;
    filtering the data representing the peripheral, non-invasive waveform through a low pass filter and a high pass filter to obtain data representing a pre-calibrated, peripheral waveform in which the patient's cardiovascular waveform features are preserved;
    using the measurements of patient's systolic blood pressure and diastolic blood pressure as measured with the brachial cuff device in oscillometric mode to calibrate the pre-calibrated, peripheral waveform resulting in a NIBP-calibrated, peripheral waveform;
    determining values for one or more parameters pertaining to the cardiovascular features of the NIBP-calibrated, peripheral waveform;
    providing multiple recalibration equations, wherein said multiple recalibration equations are determined by comparing groupings of data collected from a general population correlating NIBP-calibrated, peripheral waveform data to invasively measured peripheral pressure waveform data, wherein said groupings of data are grouped according to values for one or more parameters pertaining to cardiovascular features of the NIBP-calibrated, peripheral waveform data from the general population, wherein said collected data from the general population comprises at least peripheral waveform data, brachial systolic and diastolic blood pressure values measured in oscillometric mode using the specific type of brachial cuff that is being recalibrated, and invasively measured brachial systolic and diastolic blood pressure values;
    selecting one of the multiple recalibration equations based on the determined values for the one or more parameters pertaining to cardiovascular features of the NIBP-calibrated, peripheral waveform;
    recalibrating the NIBP-calibrated, peripheral waveform based on the selected recalibration equation to produce a recalibrated peripheral waveform; and
    estimating a value for the patient's invasively equivalent brachial systolic blood pressure as a maximum value of the recalibrated peripheral waveform and estimating a value for the patient's invasively equivalent brachial diastolic blood pressure as a minimum value of the recalibrated peripheral waveform.

11. The method as recited in claim 10 wherein the step of recording data representing the peripheral, non-invasive waveform of the patient is accomplished using a tonometer to measure a non-invasive, radial pressure pulse at the wrist of the patient.

12. The method as recited in claim 10 wherein the one or more parameters pertaining to the cardiovascular features of the NIBP-calibrated, peripheral waveform comprises multiple parameters and the multiple parameters include augmentation index, ejection duration, heartrate, and the ratio of area under the curve during diastole divided by the area under the curve during systole.

13. The method as recited in claim 10 wherein the selected recalibration equation equation is selected using a decision tree based on the determined values for the one or more parameters pertaining to cardiovascular features of the NIBP-calibrated, peripheral waveform.

14. The method as recited in claim 10 wherein the step of recording data representing the peripheral, non-invasive waveform of the patient is accomplished using an optical sensor to measure the non-invasive peripheral waveform of the patient.

* * * * *

UNITED STATES PATENT AND TRADEMARK OFFICE
CERTIFICATE OF CORRECTION

PATENT NO. : 11,006,842 B2
APPLICATION NO. : 15/907693
DATED : May 18, 2021
INVENTOR(S) : Ahmad Qasem It is certified that error appears in the above-identified patent and that said Letters Patent is hereby corrected as shown below:

In the Claims

In Claim 1, Column 13, Line 65, delete "MBP-calibrated" and insert -- NIBP-calibrated --

In Claim 2, Column 14, Line 15, delete "MBP-calibrated" and insert -- NIBP-calibrated --

In Claim 7, Column 15, Line 3, delete "Pi," and insert -- $P_i$ --

In Claim 7, Column 15, Line 5, delete "Bi," and insert -- $B_i$ --

In Claim 7, Column 15, Line 7, delete "$C_i$," and insert -- $C_i$ --

In Claim 7, Column 15, Line 27, delete "where (z)=([u(t) u(t-1) u(t-na) y(t-1) . . . y(t-nb)] × $B_i+C_i$" and insert -- where (z)=([u(t) u(t-1) . . . u(t-na) y(t-1) . . . y(t-nb) × $B_i+C_i$ --

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*